United States Patent [19]

Bowley

[11] Patent Number: 4,762,420

[45] Date of Patent: Aug. 9, 1988

[54] PHOTOMETRIC READING DEVICE FOR SEROLOGICAL ANALYSIS

[75] Inventor: Alan R. Bowley, Inverness, Scotland

[73] Assignee: Fisons plc, Ipswich, England

[21] Appl. No.: 30,176

[22] Filed: Mar. 25, 1987

[30] Foreign Application Priority Data

Apr. 1, 1986 [GB] United Kingdom ............... 86/07975

[51] Int. Cl.$^4$ ............................................. G01N 21/59
[52] U.S. Cl. ..................................... 356/436; 356/440; 422/65
[58] Field of Search ................. 356/39, 435, 440, 442, 356/246; 422/63, 65

[56] References Cited

U.S. PATENT DOCUMENTS

| | | | |
|---|---|---|---|
| 3,773,426 | 11/1973 | Mudd | 356/246 |
| 4,004,150 | 1/1977 | Natelson | 356/246 |
| 4,115,010 | 9/1978 | McAleer et l. | 356/440 |
| 4,431,307 | 2/1984 | Suovaniemi | 356/440 |
| 4,498,780 | 2/1985 | Banno et al. | 356/440 |

FOREIGN PATENT DOCUMENTS

| | | | |
|---|---|---|---|
| 2838498 | 3/1980 | Fed. Rep. of Germany | 356/442 |
| 2014300 | 8/1979 | United Kingdom | 356/442 |

*Primary Examiner*—R. A. Rosenberger
*Attorney, Agent, or Firm*—Marshall, O'Toole, Gerstein, Murray & Bicknell

[57] ABSTRACT

A photometric reading device comprises a plurality of reading elements (30), each comprising a light emitting diode and a corresponding photodiode on opposing sides of a sample pathway along which a sample microplate (10) can travel. The microplate (10) includes rows of sample wells arranged transverse to the line of relative motion of the microplate (10) and the reading elements (30).

The reading elements (30) are arranged such that, during continuous relative motion of the reading elements (30) and the microplate (10), the reading elements (30) come into registration sequentially with the wells in the first row of wells in the microplate (10), then with the wells in the second row of wells, and so on.

10 Claims, 2 Drawing Sheets

PHOTOMETRIC READING DEVICE FOR SEROLOGICAL ANALYSIS

FIELD OF THE INVENTION

This invention relates to a photometric reading device for automatically performing analytical operations on liquid samples, in particular for performing serological analysis such as is involved in, for example, blood grouping, the determination of the osmotic fragility of red blood cells, antibody titration, prothrombin tests and cross-matching tests.

DESCRIPTION OF THE PRIOR ART

One of the most important applications of serological testing is the identification of blood groups. Present methods of determining to which group (ABO or Rh(D)) blood belongs involve mixing samples of red blood cells with several different reagent antisera and observing each test to see if the red cells agglutinate, or clump together. For ABO determinations, complementary tests are performed by mixing samples of plasma with red blood cells of known antigenic specificity. The interpretation of both sets of tests must agree before an ABO group can be assigned.

Conventionally, the analysis is carried out in test tubes or even on a tile. However, this test method is tedious. Automated or semi-automated systems for ABO/Rh testing have therefore been developed which perform all of the necessary tests in the wells of a disposable called a microplate. The microplate is a clear rigid moulding of plastics material such as polystyrene in which is impressed a matrix of, for example 8×12, reaction wells. After a dilute suspension of red blood cells is mixed with appropriate antisera and plasma is mixed with red cells of known antigenic specificity, the microplate is centrifuged to pellet the red cells and then agitated to resuspend them. Cells which have agglutinated will settle to the bottom of a well within 1 to 5 minutes, while cells which have not agglutinated will remain in suspension for 10 minutes or more. Thus, a strong positive reaction is characterised by a button of agglutinated cells at the bottom of a well surrounded by a relatively clear supernatant, while a negative reaction is characterised by a uniform suspension of red cells. A weakly positive reaction is seen as small clusters of cells spread across the bottom of a well.

In such automated systems, the presence or absence of agglutination in each well of the microplate is examined optically by passing light through it and measuring the transmitted light with a photometer. The type of reaction present in a well is determined from the absorbance of the supernatant. After all of the reactions have been categorised as positive or negative, the pattern of reactions for a sample is compared to template patterns to determine the ABO/Rh test results.

In the majority of automated systems previously known, such as that disclosed in U.S. Pat. No. 3,533,744, travel of the microplate through the reader has been intermittent i.e. the microplate is advanced until the first row of wells comes into registration with the light source and the photometer, then the microplate is stopped, the absorbance is measured and the microplate advanced until the next row of wells reaches the measuring position. This moving and stopping has effectively shaken the liquid in the microplate, which, unless time is left to enable the liquid to settle, can cause disturbance of the liquid meniscus, which in turn can cause unwanted optical aberrations. Alternatively, the measurement has been made while the microplate is moving. In this case, each well of the microplate is illuminated through a very narrow transverse slit, so that the sample is scanned by a very thin transverse band of light during the movement of the sample carrier.

In these known arrangements the light beams (and the corresponding photodetectors) have been arranged in rows at right angles to the direction of movement of the microplate.

In practice a relatively powerful polychromatic light source, e.g. a tungsten filament lamp, has been used, together with expensive interference filters to remove light of unwanted wavelengths (e.g. all except the green). The light beam from the lamp has usually been split and led through optical fibres to the individual wells of the microplate, and also through comparison channels to enable fluctuations in the output of the lamp to be compensated. Alternatively, readers in which a light beam is used to read one well at a time, but using a comparison channel to take account of light variations have been used. It has also been found desirable to chop the light beams mechanically to provide a further check on the calibration of the photometers (the so called dark current comparison).

Due to the mechanical complexity of such previously known automated systems they are expensive. Furthermore, they include many moving parts and are therefore liable to mechanical failure. For these reasons, it is generally accepted that their use is justified only in large centres. Consequently smaller blood grouping laboratories have been restricted to manual methods.

We have not found an improved form of photometric reading device which overcomes or substantially mitigates these disadvantages.

BRIEF SUMMARY OF THE INVENTION

Thus, according to the invention there is provided a photometric reading device comprising a plurality of reading elements; and means of bringing about continuous motion relative to said reading elements of first and second rows of samples arranged transverse to the direction of relative motion, said reading elements being arranged to come into registration during said relative motion sequentially with the samples in the first row of samples and thereafter with the samples in the second row of samples.

The reading elements can be arranged in several ways. The arrangement is subject to only two constraints. Firstly, the reading elements must be located at different positions along the direction of relative motion of the samples and the reading elements so that the reading elements come into registration with the individual samples in each row of samples at different times. Secondly, the separation of the centres of the reading elements along the direction of relative motion must not be greater than the separation of the centres of samples in adjacent rows of samples so that all the samples in the first row of samples come into registration with the reading elements before the first of the samples in the second row of samples comes into registration with a reading element. The placing of the reading elements is otherwise not critical, but it is preferred to arrange that, assuming constant velocity of the samples, the samples come into registration with the reading elements after equally spaced intervals of time. Configurations in which the reading elements are evenly distributed impose least restriction on the size of the reading elements. The actual order in which the samples are measured is immaterial since the results may be re-arranged by subsequent data processing.

The reading elements may, for example, be arranged in a row at an acute angle to the normal to the direction of relative motion. Such an arrangement, and especially an arrangement in which alternate reading elements are staggered thereby forming two separate rows of reading elements, allows a greater area around each reading element with the consequent advantage that larger and more sensitive reading elements can be accommodated.

The magnitude of the acute angle depends on the length of the rows of samples and on the separation of thew centres of samples in adjacent rows of samples. The angle is typically less than 20°, usually less than 10°, and particularly approximately 5°.

The continuous relative motion of the samples enables the individual measurements to be spread evenly within the time spent by the samples within the device. As a result the speed of operation of the device can be enhanced.

The relative motion of the samples with respect to the light sources can be effected by moving the samples with respect to stationary light sources or by moving the light sources with respect to stationary samples.

We prefer the samples to be contained in a microplate, e.g. a rectangular microplate containing 8×12 sample wells. When such a microplate is used then, if the direction of motion of the microplate relative to the reading elements is parallel to the long axis of the microplate, there are 12 rows of 8 samples to be measured. On the other hand, if the direction of motion of the microplate relative to the reading elements is parallel to the short axis of the microplate, then there are 8 rows of 12 samples. The sample wells are preferably round-bottomed.

We prefer the number of reading elements to be the same as the number of samples in each row of samples i.e. corresponding samples in each row of samples are measured by the same reading element.

The reading elements preferably comprise a plurality of light sources and a corresponding plurality of light detecting means. The light detecting means are preferably photodetectors, e.g. photodiodes.

Light sources which are particularly suitable for use in the device of the invention are light emitting diodes (LEDs). LEDs have rapid on/off characteristics which enable the samples to be moved continuously and smoothly between a collection of LEDs and corresponding photodetectors, the arrangement of the LEDs and photodetectors being such that each LED and its corresponding photodiode is activated for a very brief time at the time when the appropriate sample is in its optimum position for examination. The very rapid on/off characteristics of the LEDs and the provision of an LED for each sample (as opposed to one part of a split beam), enables the LEDs to be activated individually so that there is no scattered light interference from one sample to another. The effect of moving the samples during the finite time of measurement is to "smear" out the beam, but this is made acceptable by the very short response time of the LEDs.

Thus, according to a further aspect of the invention, there is provided a photometric reading device comprising a sample pathway;
means of bringing about motion of a sample microplate along said sample pathway;
light detecting means;
and
a plurality of light emitting diodes;
said plurality of light emitting diodes and said light detecting means being arranged on opposing sides of said sample pathway.

If any agglutinate is allowed to obstruct any part of the light beam a high absorbance will result, which will be interpreted as negative. To ensure that this does not happen the samples are tilted, e.g. to an angle of 17° to the horizontal, so that the agglutinate collects in one part of the well. Alternatively, a horizontal microplate containing wells provided with V-shaped, U-shaped or inclined bases may be used.

It is preferred to position the light sources such that during measurement the measurement beam does not pass through the part of the sample where agglutinate has collected. Also, the effective diameter of the beam is preferably small relative to the sample diameter. This helps to ensure that there is good discrimination in the measurement between positive and negative reactions.

When the light passing through a sample is detected and measured it is necessary to subtract from the result the "dark current" for that particular detector. The latter will be affected by any stray light that can penetrate the measurement area, so that usually it is necessary to take special care to exclude all ambient light. The use of LEDs with their rapid switching allows a "dark current" measurement to be made just before each light transmission measurement so that the final result is essentially insensitive to variation in ambient light.

The LEDs preferably produce substantially monochromatic (e.g. ±20 nm bandwidth) light of a wavelength susceptible to absorption by the liquid to be tested, e.g. the wavelength of the light should be in the green region of the spectrum (ca 570 nm) when the liquid comprises blood cells.

LEDs consume very much less electrical power than filament bulbs. Thus the heat dissipated within the equipment is considerably reduced and power supplies may be simple, small and inexpensive. Furthermore LEDs have a long life and are unlikely to need replacement within the life of the instrument. In certain embodiments of the invention the LEDs are used in pulsed mode and are each switched on for only about five milliseconds for each sample measured. Thus the total switch-on time for each LED during a year's typical use might be only ten minutes. By way of contrast filament bulbs must be run continuously whilst the instrument is switched on. LEDs also have emission characteristics which are extremely stable and their use can enable comparison channels to be dispensed with. LEDs are also physically small and may thus be contained in the space immediately adjacent to each vessel, thereby obviating the need for fibre optics in multi-channel designs.

The LED is preferably such that it reaches full intensity from "off" (and vice versa) very rapidly, e.g. within 500 nanoseconds. This allows measurements to be made in rapid succession for both states of the LED, i.e. both on and off. High speed measurement also allows reading while the sample is moving without significantly broadening the effective measuring beam width.

The light detecting means may be a conventional photodiode and preferably a photodiode having a high sensitivity at the emission wavelength of the LED, a small physical size, a sensitive area large enough that all light emerging from the sample is detected (the light beam may be focussed onto the photodiode by a lens), and a rapid response matching the "on/off" characteristics of the LED.

The means of activating the LEDs, of bringing about relative motion of the samples and the reading elements and of measuring the transmitted light may be coupled with conventional control and data processing apparatus, e.g. an analog to digital converter and a microcomputer.

DESCRIPTION OF PREFERRED EMBODIMENTS OF THE INVENTION

A photometric reading device for use in the determination of blood groups comprises a photometric reading head and a sample drive adapted to transport a sample microplate through the reading head.

Figure 1:
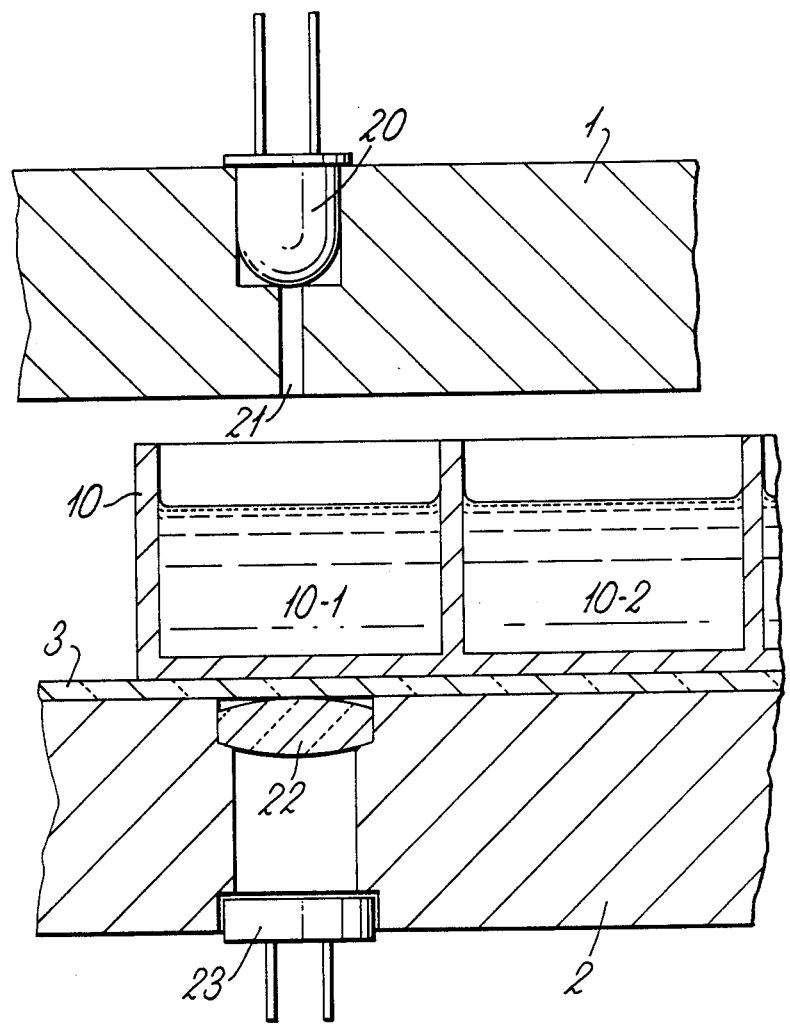
FIG. 1 is a detailed view in section of one element of a photometric reading head.

The reading head comprises an upper plate (1) and a base plate (2), into which are set respectively the light-emitting and light-receiving parts of twelve photometric reading elements. As shown in FIG. 1, each element comprises, in the upper plate, a light-emitting diode or LED (20) and a parallel hole collimator (21), and, in the base plate, a condenser lens (22) and a photodiode (23). The base plate (2) is covered by a glass screen (3). The LED (20) emits a beam of green, substantially monochromatic light of wavelength 570 nm. The beam has a diameter of approximately 2 mm within the wells.

The reading head is tilted at 17° to the horizontal to encourage any agglutinate contained within the wells (10-1, 10-2 etc.) of the sample microplate (10) to move out of the measurement beam which is offset from the central axis of the microplate well (10-1, 10-2 etc.).

A microplate drive (not shown) is adapted to convey a rectangular, 96-well sample microplate (10) through the photometric reading head. The microplate drive comprises a carriage driven by a stepper motor via a reduction gearbox, pulleys and a drive cord.

The wells (10-1, 10-2 etc.) of the microplate (10) are arranged in eight rows of twelve. The elements of the reading head are arranged such that, as the microplate (10) passes through the head, corresponding wells in each row of wells (10-1, 10-2 etc.) are scanned by one of the reading elements.

Figure 2:
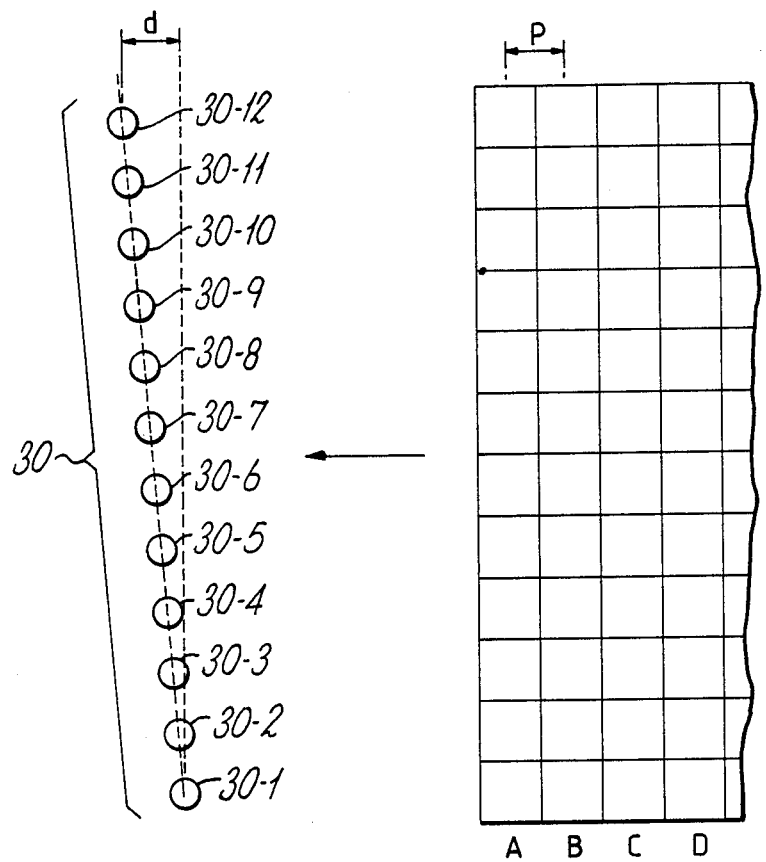
FIG. 2 shows the arrangement of a set of such photometric reading head elements in relation to the direction of motion of a sample microplate.

In FIG. 2 the arrangement of the reading elements (30) with respect to the direction of motion of the sample microplate (10) is shown. The microplate (10) is moved in the direction of the arrow past a row of reading elements (30) arranged in a line at an angle of approximately 5° to the normal to the direction of motion of the microplate (10). In an alternative arrangement (not shown) the reading elements (30) are staggered in two parallel rows at a similar angle. This alternative arrangement provides maximum space (and hence minimum interference between the elements and maximum flexibility in choice of devices for the units).

The distance d (the separation along the axis of motion of the microplate (10) of the first and last of the reading elements (30) to come into registration with a well in the microplate (10)) is slightly less than the distance p, the separation of the centres of the wells in adjacent rows of the microplate (10). In preferred embodiments of the device, the distance d is approximately equal to $[(n-1)/n].p$ where n is the number of reading elements i.e. in the case of the device illustrated here d is approximately $(11 \times p)/12$.

In operation the microplate (10) is inserted into the carriage and the reading sequence initiated. As each row of wells A, B, C, D etc. in the microplate (10) passes through the reading head, the reading elements are fired in the order 30-1, 30-2, 30-3, 30-4, 30-5, 30-6, 30-7, 30-8, 30-9, 30-10, 30-11, 30-12. The absorbance of the supernatant in each sample well is measured and transmitted to a host computer (not shown).

Prior to measurement, the microplate (10) may be identified by an attached bar code label. In this case, a separate hand wanded bar code reader (not shown) is used to read the label and transmit the decoded number back to the host computer. A photoelectric trigger at the label position ensures that the only codes accepted are from microplates placed in the instrument's carriage. A successful label read initiates the reading sequence and prevents the microplate from being exchanged.

In an alternative embodiment to that described above, eight reading elements are used and the microplate is moved along a line parallel to its long axis. This arrangement has the advantage that the number of components, and hence the cost, is lower. The total measurement time, however, is somewhat longer (if the speed of relative motion of the microplate and the reading elements is the same).

I claim:
1. A photometric reading device comprising
a plurality of reading elements; and
means of bringing about continuous motion relative to said reading elements of first and second rows of samples arranged transverse to the direction of relative motion,
said reading elements being arranged to come into registration during said relative motion sequentially with the samples in the first row of samples and thereafter with the samples in the second row of samples.

2. A photometric reading device according to claim 1, wherein said reading elements are arranged in a row at an acute angle to the normal to the direction of relative motion of said reading elements and said samples.

3. A photometric reading device according to claim 2, wherein said acute angle is less than 20°.

4. A photometric reading device according to claim 1, wherein said reading elements are arranged alternately on two parallel rows at an acute angle to the normal to the direction of relative motion of said reading elements and said samples.

5. A photometric reading device according to claim 4, wherein said acute angle is less than 20°.

6. A photometric reading device according to claim 1, wherein said reading elements comprise a plurality of light sources and a corresponding plurality of light detecting means.

7. A photometric reading device according to claim 6, wherein said light sources are light emitting diodes.

8. A photometric reading device according to claim 6, wherein said light detecting means are photodiodes.

9. A photometric reading device according to claim 6, wherein said light sources are substantially monochromatic.

10. A photometric reading device according to claim 6, wherein the light emitted by the light sources is green.

* * * * *